US008450098B2

(12) United States Patent
Kim et al.

(10) Patent No.: US 8,450,098 B2
(45) Date of Patent: May 28, 2013

(54) METHOD FOR INTRODUCING NUCLEIC ACIDS INTO FUNGAL CELLS

(75) Inventors: Steven Kim, Fremont, CA (US); Andrei Miasnikov, Mountain View, CA (US)

(73) Assignee: Danisco US Inc., Palo Alto, CA (US)

( * ) Notice: Subject to any disclaimer, the term of this patent is extended or adjusted under 35 U.S.C. 154(b) by 7 days.

(21) Appl. No.: 12/600,452

(22) PCT Filed: May 21, 2008

(86) PCT No.: PCT/US2008/006509
§ 371 (c)(1),
(2), (4) Date: Aug. 23, 2010

(87) PCT Pub. No.: WO2008/153712
PCT Pub. Date: Dec. 18, 2008

(65) Prior Publication Data
US 2010/0304468 A1   Dec. 2, 2010

Related U.S. Application Data

(60) Provisional application No. 60/931,072, filed on May 21, 2007.

(51) Int. Cl.
*C12N 1/00* (2006.01)
*C12N 3/00* (2006.01)
*C12N 1/20* (2006.01)
*C12N 15/01* (2006.01)
*C12N 15/02* (2006.01)
*C12M 1/42* (2006.01)

(52) U.S. Cl.
USPC ............ 435/254.1; 435/254.6; 435/242; 435/253.3; 435/446; 435/450; 435/285.2

(58) Field of Classification Search
None
See application file for complete search history.

(56) References Cited

U.S. PATENT DOCUMENTS

| 4,683,195 A | 7/1987 | Mullis et al. |
| 5,874,276 A | 2/1999 | Fowler et al. |
| 2008/0229514 A1 * | 9/2008 | Poulose et al. ............ 8/138 |

FOREIGN PATENT DOCUMENTS

| EP | 0 215 594 | 3/1987 |
| WO | WO 02/092757 A2 * | 11/2002 |
| WO | WO 2005/001036 A2 | 1/2005 |
| WO | WO 2006/043178 A2 | 4/2006 |
| WO | WO 2008/153712 | 12/2008 |

OTHER PUBLICATIONS

Heard et al., (The Journal of General Physiology, 1960; vol. 43: 635-654).*
Chakraborty et al. (Canadian Journal of Microbiology, 1991; 37(11): 858-863).*
Boel, E. et al. "Two different types of intervening sequences in the glucoamylase gene from *Aspergillus niger*." *EMBO J.* 3(7):1581-1585, 1984.
Brosius, J. "Superpolylinkers in cloning and expression vectors." *DNA (Mary Ann Liebert, Inc.)* 8(10):759-777, 1989.
Cao, Q.N. et al. "Penicillopepsin-JT2, a recombinant enzyme from *Penicillium janthinellum* and the contribution of a hydrogen bond in subsite S3 to k(cat)." *Protein Sci* 9(5):991-1001, 2000.
Chakraborty, B.N. et al. "An electroporation-based system for high-efficiency transformation of germinated conidia of filamentous fungi." *Canadian Journal of Microbiology* 37(11):858-863, 1991.
Faber, K.N. et al. "Highly-efficient electrotransformation of the yeast *Hansenula polymorpha*." *Current Genetics* 25(4):305-310, 1994.
Goldman, G. H. et al. "Transformation of *Trichoderma harzianum* by high-voltage electric pulse." *Current Genetics* 17(2):169-174, 1990.
Hartley, J.L. et al. "DNA cloning using in vitro site-specific recombination." *Genome Research* 10(11):1788-1795, 2000.
Jiang, Q. et al. "Enhanced frequency of *Beauveria bassiana* blastospore transformation by restriction enzyme-mediated integration and electroporation." *Journal of Microbiological Methods* 69(3):512-517, 2007.
Kelly, J.M. et al. "Transformation of *Aspergillus niger* by the amdS gene of *Aspergillus nidulans*." *The EMBO Journal* 4(2):475-479, 1985.
Margolin, B.S. et al. "Improved plasmids for gene targeting at the his-3 locus of *Neurospora crassa* by electroporation." *Fungal Genet. Newsletter* 44:34-36, 1997.
May, G. "Fungal Technology." In *Applied Molecular Genetics of Filamentous Fungi*, eds. J.R. Kinghorn et al. Glasgow, UK: Blackie Academic & Professional, pp. 1-27, 1992.
Mullaney, E.J. et al. "Primary structure of the trpC gene from *Aspergillus nidulans*." *Molecular and General Genetics MGG* 199(1):37-45, 1985.
Nevalainen, K.M.H. et al. "The Molecular Biology of *Trichoderma* and its Application to the Expression of Both Homologous and Heterologous Genes." In *Molecular Industrial Mycology*, eds. S.A. Leong et al. New York: Marcel Dekker, pp. 129-148, 1991.
Ninomiya, Y. et al. "Highly efficient gene replacements in *Neurospora* strains deficient for nonhomologous end-joining." *PNAS* 101(33):12248-12253, 2004.
Nunberg, J.H. et al. "Molecular cloning and characterization of the glucoamylase gene of *Aspergillus awamori*." *Mol. Cell. Biol.* 4(11):2306-2315, 1984.
Penttilä, M. et al. "A versatile transformation system for the cellulolytic filamentous fungus *Trichoderma reesei*." *Gene* 61(2):155-64, 1987.
Richey, M.G. et al. "Transformation of Filamentous Fungi with Plasmid DNA by Electroporation." *Phytopathology* 79(8):844, 1989.
Ruiz-Diez, B. "Strategies for the transformation of filamentous fungi." *Journal of Applied Microbiology* 92(2):189-195, 2002.
Sanchez, O. et al. "Efficient transformation of *Aspergillus nidulans* by electroporation of germinated conidia." *Fungal Genet. Newsletter* 43:48-51, 1996.
Schiestl, R.H. et al. "Introducing DNA into Yeast by Transformation." *Methods* 5(2):79-85, 1993.
Yelton, M.M. et al. "Transformation of *Aspergillus nidulans* by using a trpC plasmid." *Proc. Natl. Acad. Sci. U.S.A* 81(5):1470-4, 1984.

(Continued)

*Primary Examiner* — Vanessa L. Ford
*Assistant Examiner* — Lakia Tongue
(74) *Attorney, Agent, or Firm* — Danisco US Inc.

(57) ABSTRACT

The method disclosed herein, relates generally to introducing molecules such as biomolecules (e.g., nucleic acids) into a filamentous fungus. More specifically, the methods disclosed herein relate to introducing one or more nucleic acids into a filamentous fungus.

17 Claims, 6 Drawing Sheets

OTHER PUBLICATIONS

Douglas C. Vann, Poster 27,"Electroporation-based Transformation of Freshly Harvested Conidia of *Neurospora Crassa*," 18$^{th}$ Fungal Genetices Conference, Mar. 21-26, 1995, Asilomar Conference Center, Pacific Grove, California, www.fgsc.net/asil95/poster2.html.

International Search Report for International Application No. PCT/US2008/006509 published dated Dec. 4, 2008.

Van Den Hondel, C.A.M.J.J., et al., "Heterologous Gene Expression in Filamentous Fungi." In *More Gene Manipulations in Fungi*, J.W. Bennett, et al., eds., Academic Press, pp. 396-428, 1991.

\* cited by examiner

*als* Gene Fragment

```
GGCGCGCCTGAGACAATGGCCGGCAATGGTAAAAAGGACCAAGATGTACTAGGTAGTTGCAATG
TGGCTTATTACCTACCTACTACCTGGTAGGCACCTACTAGGTACTTGGGTAGACGGACAATGAA
ATTTGAAGTCGGGGTTGCAGGAAAGCAGGGCGCTGGACACATTGTGCTTCAGGCGGTACCCGTC
GTCATCGTCAGCCAATGTCGAGGCCCGGCAGCCCGAGGAGCGAGACAACCTTGGCCGGAGGAGC
CCGCAGGTACCTGCCAAAGCGCGGCTGGTACCTCTCAACCCTCTCAGGCCTGTTGGATGCCCTA
TGACATGCCCTGGGGGATGCAGCTGTTGCCCCGGCCCCGCACTTTCGGGTGACCGCGAGGCTGC
TGATTGGCTGGTTGCCACGGGCTGGGCGGTCCCTGAAGTTGTTGCCATCTGAACTCTGTCGGCG
CTGGCGTCGGCTGCGCCCAATGGGAGGCGAGACAACTCAGGGTACTAGAATCACTGACAGAAGA
AGAGAATCGAAAGTAGGTAGACAGCCAATTCGTTGCATGGCAGGCAACCGCACAGGAGAAAAAT
TGACTACCCCACAATCAGGCACAGTAAGTAGGGCACAGTACGTATGTACAGACAAGGCGCAAGC
GATACTGCGCGACCCGGTACCTCGCCGGCTTGACACGTGCGACAGGCTACTTTACTAGTATTCG
CAGCGGCGGGTCGCGCATTATTACATGTACTGTGCCGCCATTTGATGACTGGGCTGCTGCAGTA
TTAGTAGATCTGCCCGGCATCGCCCTNNNNNNNNNNNNNNNNNNNNNNNNNNNNNNNNNNNNNNN
NNNNNNNNNNNNNNATTCGTCAGAGAGGAAAAGACGAGAAAAAAAGGGCAGCAGAGACGTCGGTC
TGGCTCACGTGCTGCATCTCTGCGCACTCTCATTTTTTTTATTGTCCGACCCCTCCCTCAACCT
TCTCCTTCGTTGACAGGCTAAGCCTTGCTTCGACGCTCTCTCTTTGAATTTTTCTACTTCTACC
TTCTTTTCTTGCGTGTTACCCACCATAGCTCGATTCACGATGCTCCGAAGTCGCCAAGTCACAG
CCAGGGCCGTCCGGGCTCTGGGCCAGGCGCGCGCCTTTACCTCGACGACCAAGCCTGTCATGAT
CCAGAGCAGCCAGAGGAAACAGGCCAACGCCAGCGCTGCTCCGTAAGTCGCCCATTGCCATTGC
ATCTTCTGTTTGATATATACTTCCTGCTGCTTGCGTGGCGTCGTCTCTCGGTTATGCGTGTCAA
GGACCAGGTGTGTTCGCATCGTGGTTTTCCAGCGCCGATTACCGGGGACGAATTTTTGGCTGC
TCAACTCGCGCGCGCATTCTGATTCTTCGTTTTCAATCTTGAGCGACAACTGGCTAACATAA
TGGCCATTGGCAATTGCTTCACACAGACAAGTCCGCCCTGTACCGAGCCCTGCTTTCAACGCTG
AAGACAAAGACCGCAGCCATGTGCAGCCTCTGGTCAACCCGTCGAAGCCCGACATGGATGAATC
GTATGTCCACGTCCCCTCGTCCCGCCCTACAAAATGAACACGATTACACCAGAATTTTTGCAAC
AATCGACACTTCTATAACAGACCAATTGAGCTTTGTTCTGACCAATCATGTTGCTCTAGATTCA
TTGGCAAAACCGGAGGCGAAATCTTCCACGAGATGATGCTGCGACAGGGTGTCAAGCACATTTG
TAGGTTCCGATGCCGGCCGCCCACACGGGCTCCATCCTTGCTCCATCTCTCCAGCTAGGCAAAT
CTCGCTAACCTTGAGTCACCATCCAGTCGGATACCCTGGCGGCGCTATCCTGCCCGTCTTCGAC
GCCATCTACAACTCAAAACACTTCGACTTCATCCTGCCCCGTCATGAGCAGGGAGCTGGCCATA
TGGCCGAGGGCTATGCCCGTGCCTCGGGCAAACCCGGTGTCGTCCTGGTGACTTCCGGCCCCGG
TGCTACCAATGTCATCACGCCCATGCAGGATGCCCTGTCGGACGGAACGCCCTTGGTCGTCTTC
TGCGGCCAGGTCCCCACCACGGCCATCGGCAGCGATGCCTTCCAAGAGGCCGACGTCGTGGGCA
TCTCGCGGGCCTGCACCAAGTGGAACGTCATGGTCAAGAGCGTTGCTGAGCTGCCGCGGAGAAT
CAACGAGGCCTTTGAGATTGCCACCAGCGGCCGCCCTGGCCCCGTCCTCGTCGACCTGCCCAAG
GATGTCACGGCTGGTATCCTGAGGAGAGCCATCCCTACGGAGACTGCTCTGCCGTCTCTGCCCA
GTGCCGCCTCCCGCGCCGCCATGGAGCTGAGCTCCAAGCAGCTCAACGCCTCCATCAAGCGTGC
CGCCGACCTCATCAACATCGCCAAGAAGCCCGTCATCTACGCCGGTCAGGGTGTCATCCAGTCC
GAGGGCGGCGTTGAGCTCCTGAAGCAGCTGGCGGACAAGGCCTCCATCCCCGTCACCACCACCC
TCCATGGCCTGGGTGCCTTTGATGAGCTGGACGAGAAGTCGCTGCACATGCTGGGCATGCACGG
```

*FIG. 5A* als Gene Fragment

```
CTCGGCGTATGCCAACATGGCCATGCAGCAGGCCGACCTCATCATCGCCCTCGGCAGCCGATTC
GACGACCGTGTTACTCTGAATGTCTCCAAATTTGCGCCTGCAGCCAGGCAAGCTGCTGCCGAGG
GCCGCGGCGGCATCATTCACTTTGAGATCATGCCCAAGAACATCAACAAGGTCATCCAGGCGAC
CGAGGCCGTCGAGGGCGACGTCGCCACCAACCTGAAGCACCTCATTCCCCAGATTGCCGAAAAG
TCCATGGCGGACCGAGGAGAGTGGTTCGGCCTCATCAATGAGTGGAAGAAGAAGTGGCCCCTGT
CAAACTACCAGCGCGCGGAGCGGGCTGGCCTCATCAAGCCGCAGACGGTCATGGAGGAGATTAG
CAACCTGACGGCCAACCGAAAGGACAAGACGTACATTGCCACGGGTGTCGGCCAGCACCAGATG
TGGGTTGCCCAGCACTTCCGCTGGAGGCACCCTCGATCCATGATTACCTCTGGTGGTCTGGGCA
CCATGGGCTACGGTCTCCCCGCGGCCATTGGCGCCAAGGTGGCCCAGCCCGACGCTCTCGTAAT
TGACGTTGATGGCGATGCCTCGTTTAACATGACGCTGACGGAGCTGTCGACTGCTGCACAGTTC
AACATTGGCGTCAAGGTGGTTGTGCTCAACAACGAGGAGCAGGGCATGGTGACGCAGTGGCAGA
ACCTCTTTTACGAGGACCGATATGCCCACACGCACCAGAAGAACCCCGACTTCATGAAGCTGGC
CGACGCCATGGGCGTTCAGCACCAGCGCGTGACGGAGCCGGAGAAGCTGGTCGATGCCCTGACG
TGGCTGATCAACACCGATGGCCCCGGCCCTGTTGGAGGTTGTCACGGACAAGAAGGTGCCTGTCC
TGCCCATGGTGCCCGCCGGATCGGCCCTGCACGAGTTCCTCGTCTTTGAACCTGGTGAGTCTAC
TTCAGACATATTGCTTGCGCATTGCAGATACTAACACTCTCACAGAAAAGGATAAGCAGCGCCG
TGAGCTGATGAAGGAGAGAACAAAGGGTGTGCACTCCTAAAGCGATGATGTCTGCGAGGGGTTC
TTCGTTGAACCCTAGTTCAGGCACCATCTTACCCTCTTATTTTTTCCCGTGGGCTTTCATTTTG
TGTCATCCGAGCATGACGTTGTAGGGTTGGAGTTTCTTCCTTTTTATCTTGTCATTTACTGGTA
CCCATAGGCGCGAGACTAGGCTTCCATGTTTTGTTTTGCGACTTTCAAAAAGTACTTTTAGTGG
TTTGGGGCACGACGAGGGGGGGCAACCTCTTCTGTCGAAAAAGGTGGCTGGATGGATGAGATGA
GATGAGATGAGGGTGAAGATAGATACCTGCAGTGTTTTTGACGCGACGGGATGGCGATCGC
```

FIG. 5B

Lanes:
2) Marker X (Roche)
3) #40 SK783 vs SK784
4) #41 SK783 vs SK784
5) Marker X (Roche)
6) #40 675F vs SK784
7) #41 675F vs SK784
8) #40 SK783 vs 678R
9) #41 SK783 vs 678R Lanes:
1) Mark 12 Standard (Invitrogen)
2) C Control Strain
3) Transformant #41 with cbh1 Deletion

SEQUENCE LISTING

<160> NUMBER OF SEQ ID NOS: 16

<210> SEQ ID NO 1
<211> LENGTH: 413
<212> TYPE: PRT
<213> ORGANISM: Buttiauxella sp.

<400> SEQUENCE: 1

```
Asn Asp Thr Pro Ala Ser Gly Tyr Gln Val Glu Lys Val Val Ile Leu
1               5                   10                  15

Ser Arg His Gly Val Arg Ala Pro Thr Lys Met Thr Gln Thr Met Arg
                20                  25                  30

Asp Val Thr Pro Asn Thr Trp Pro Glu Trp Pro Val Lys Leu Gly Tyr
            35                  40                  45

Ile Thr Pro Arg Gly Glu His Leu Ile Ser Leu Met Gly Gly Phe Tyr
        50                  55                  60

Arg Gln Lys Phe Gln Gln Gly Ile Leu Ser Gln Gly Ser Cys Pro
65                  70                  75                  80

Thr Pro Asn Ser Ile Tyr Val Trp Thr Asp Val Ala Gln Arg Thr Leu
                85                  90                  95

Lys Thr Gly Glu Ala Phe Leu Ala Gly Leu Ala Pro Gln Cys Gly Leu
            100                 105                 110

Thr Ile His His Gln Gln Asn Leu Glu Lys Ala Asp Pro Leu Phe His
        115                 120                 125

Pro Val Lys Ala Gly Ile Cys Ser Met Asp Lys Thr Gln Val Gln Gln
    130                 135                 140

Ala Val Glu Lys Glu Ala Gln Thr Pro Ile Asp Asn Leu Asn Gln His
145                 150                 155                 160

Tyr Ile Pro Ser Leu Ala Leu Met Asn Thr Thr Leu Asn Phe Ser Lys
                165                 170                 175

Ser Pro Trp Cys Gln Lys His Ser Ala Asp Lys Ser Cys Asp Leu Gly
            180                 185                 190

Leu Ser Met Pro Ser Lys Leu Ser Ile Lys Asp Asn Gly Asn Glu Val
        195                 200                 205

Ser Leu Asp Gly Ala Ile Gly Leu Ser Ser Thr Leu Ala Glu Ile Phe
    210                 215                 220

Leu Leu Glu Tyr Ala Gln Gly Met Pro Gln Ala Ala Trp Gly Asn Ile
225                 230                 235                 240

His Ser Glu Gln Glu Trp Ala Leu Leu Leu Lys Leu His Asn Val Tyr
                245                 250                 255

Phe Asp Leu Met Glu Arg Thr Pro Tyr Ile Ala Arg His Lys Gly Thr
            260                 265                 270

Pro Leu Leu Gln Ala Ile Ser Asn Ala Leu Asn Pro Asn Ala Thr Glu
        275                 280                 285
```

```
Ser Lys Leu Pro Asp Ile Ser Pro Asp Asn Lys Ile Leu Phe Ile Ala
        290                 295                 300

Gly His Asp Thr Asn Ile Ala Asn Ile Ala Gly Met Leu Asn Met Arg
305                 310                 315                 320

Trp Thr Leu Pro Gly Gln Pro Asp Asn Thr Pro Pro Gly Gly Ala Leu
                325                 330                 335

Val Phe Glu Arg Leu Ala Asp Lys Ser Gly Lys Gln Tyr Val Ser Val
            340                 345                 350

Ser Met Val Tyr Gln Thr Leu Glu Gln Leu Arg Ser Gln Thr Pro Leu
        355                 360                 365

Ser Leu Asn Gln Pro Ala Gly Ser Val Gln Leu Lys Ile Pro Gly Cys
    370                 375                 380

Asn Asp Gln Thr Ala Glu Gly Tyr Cys Pro Leu Ser Thr Phe Thr Arg
385                 390                 395                 400

Val Val Ser Gln Ser Val Glu Pro Gly Cys Gln Leu Gln
                405                 410

<210> SEQ ID NO 2
<211> LENGTH: 20
<212> TYPE: PRT
<213> ORGANISM: Trichoderma reesei

<400> SEQUENCE: 2

Met Gln Thr Phe Gly Ala Phe Leu Val Ser Phe Leu Ala Ala Ser Gly
1               5                   10                  15

Leu Ala Ala Ala
            20

<210> SEQ ID NO 3
<211> LENGTH: 60
<212> TYPE: DNA
<213> ORGANISM: Trichoderma reesei

<400> SEQUENCE: 3
atgcagacct tggagctttt tctcgtttcc ttcctcgccg ccagcggcct ggccgcggcc     60

<210> SEQ ID NO 4
<211> LENGTH: 3965
<212> TYPE: DNA
<213> ORGANISM: Trichoderma reesei
<220> FEATURE:
<221> NAME/KEY: misc_feature
<222> LOCATION: (795)..(844)
<223> OTHER INFORMATION: n is a, c, g, or t

<400> SEQUENCE: 4
ggcgcgcctg agacaatggc cggcaatggt aaaaaggacc aagatgtact aggtagttgc     60
aatgtggctt attacctacc tactacctgg taggcaccta ctaggtactt gggtagacgg    120
acaatgaaat ttgaagtcgg ggttgcagga aagcagggcg ctggacacat tgtgcttcag    180
gcggtacccg tcgtcatcgt cagccaatgt cgaggcccgg cagcccgagg agcgagacaa    240
ccttggccgg aggagcccgc aggtacctgc caaagcgcgg ctggtacctc tcaaccctct    300
caggcctgtt ggatgcccta tgacatgccc tggggatgc agctgttgcc ccggccccgc    360
actttcgggt gaccgcgagg ctgctgattg gctggttgcc acgggctggg cggtccctga    420
agttgttgcc atctgaactc tgtcggcgct ggcgtcggct gcgcccaatg ggaggcgaga    480
caactcaggg tactagaatc actgacagaa gaagagaatc gaaagtaggt agacagccaa    540
ttcgttgcat ggcaggcaac cgcacaggag aaaaattgac taccccacaa tcaggcacag    600
```

```
taagtagggc acagtacgta tgtacagaca aggcgcaagc gatactgcgc gacccggtac      660
ctcgccggct tgacacgtgc gacaggctac tttactagta ttcgcagcgg cgggtcgcgc      720
attattacat gtactgtgcc gccatttgat gactgggctg ctgcagtatt agtagatctg      780
cccggcatcg ccctnnnnnn nnnnnnnnnn nnnnnnnnnn nnnnnnnnnn nnnnnnnnnn      840
nnnnattcgt cagagaggaa aagacgagaa aaaaagggc agcagagacg tcggtctggc       900
tcacgtgctg catctctgcg cactctcatt ttttttattg tccgacccct ccctcaacct      960
tctccttcgt tgacaggcta agccttgctt cgacgctctc tctttgaatt tttctacttc     1020
taccttcttt tcttgcgtgt tacccaccat agctcgattc acgatgctcc gaagtcgcca     1080
agtcacagcc agggccgtcc gggctctggg ccaggcgcgc gcctttacct cgacgaccaa     1140
gcctgtcatg atccagagca gccagaggaa acaggccaac gccagcgctg ctccgtaagt     1200
cgcccattgc cattgcatct tctgtttgat atatacttcc tgctgcttgc gtggcgtcgt     1260
ctctcggtta tgcgtgtcaa ggaccaggtg tgttcgcatc gtggttttcc agcgccgatt     1320 accggggac gaattttttgg ctgctcaact cgcgcgcgcg cattctgatt cttcgttttc      1380
aatcttgagc gacaactggc taacataatg gccattggca attgcttcac acagacaagt     1440
ccgccctgta ccgagccctg ctttcaacgc tgaagacaaa gaccgcagcc atgtgcagcc     1500
tctggtcaac ccgtcgaagc ccgacatgga tgaatcgtat gtccacgtcc cctcgtcccg     1560
ccctacaaaa tgaacacgat tacaccagaa ttttttgcaac aatcgacact tctataacag    1620
accaattgag ctttgttctg accaatcatg ttgctctaga ttcattggca aaaccggagg     1680
cgaaatcttc cacgagatga tgctgcgaca gggtgtcaag cacatttgta ggttccgatg     1740
ccggccgccc acacgggctc catccttgct ccatctctcc agctaggcaa atctcgctaa     1800
ccttgagtca ccatccagtc ggatacccctg gcggcgctat cctgcccgtc ttcgacgcca    1860
tctacaactc aaaacacttc gacttcatcc tgccccgtca tgagcaggga gctggccata    1920
tggccgaggg ctatgcccgt gcctcgggca aacccggtgt cgtcctggtg acttccggcc    1980
ccggtgctac caatgtcatc acgcccatgc aggatgccct gtcggacgga acgcccttgg    2040
tcgtcttctg cggccaggtc cccaccacgg ccatcggcag cgatgccttc caagaggcc     2100 acgtcgtggg catctcgcgg gcctgcacca agtggaacgt catggtcaag agcgttgctg    2160
agctgccgcg gagaatcaac gaggcctttg agattgccac cagcggccgc cctgcccccg    2220
tcctcgtcga cctgcccaag gatgtcacgg ctggtatcct gaggagagcc atccctacgg    2280
agactgctct gccgtctctg cccagtgccg cctcccgcgc cgccatggag ctgagctcca    2340
agcagctcaa cgcctccatc aagcgtgccg ccgacctcat caacatcgcc aagaagcccg    2400
tcatctacgc cggtcagggt gtcatccagt ccgagggcgg cgttgagctc ctgaagcagc    2460
tggcggacaa ggcctccatc cccgtcacca ccaccctcca tggcctgggt gcctttgatg    2520
agctggacga gaagtcgctg cacatgctgg gcatgcacgg ctcggcgtat gccaacatgg    2580
ccatgcagca ggccgacctc atcatcgccc tcggcagccg attcgacgac cgtgttactc    2640
tgaatgtctc caaatttgcg cctgcagcca ggcaagctgc tgccgagggc cgcggcggca    2700
tcattcactt tgagatcatg cccaagaaca tcaacaaggt catccaggcg accgaggccg    2760
tcgagggcga cgtcgccacc aacctgaagc acctcattcc ccagattgcc gaaagtccaa    2820
tggcggaccg aggagagtgg ttcggcctca tcaatgagtg gaagaagaag tggcccctgt    2880
caaactacca gcgcgcggag cgggctggcc tcatcaagcc gcagacggtc atggaggaga    2940 ttagcaaccct gacggccaac cgaaaggaca agacgtacat tgccacgggt gtcggccagc    3000
```

```
accagatgtg ggttgcccag cacttccgct ggaggcaccc tcgatccatg attacctctg    3060
gtggtctggg caccatgggc tacggtctcc ccgcggccat ggcgccaag gtggcccagc     3120 ccgacgctct cgtaattgac gttgatggcg atgcctcgtt taacatgacg ctgacggagc    3180
tgtcgactgc tgcacagttc aacattggcg tcaaggtggt tgtgctcaac aacgaggagc    3240
agggcatggt gacgcagtgg cagaacctct tttacgagga ccgatatgcc cacacgcacc    3300
agaagaaccc cgacttcatg aagctggccg acgccatggg cgttcagcac cagcgcgtga    3360
cggagccgga gaagctggtc gatgccctga cgtggctgat caacaccgat ggcccggccc    3420
tgttggaggt tgtcacggac aagaaggtgc ctgtcctgcc catggtgccc gccggatcgg    3480
ccctgcacga gttcctcgtc tttgaacctg gtgagtctac ttcagacata ttgcttgcgc    3540
attgcagata ctaacactct cacagaaaag gataagcagc gccgtgagct gatgaaggag    3600
agaacaaagg gtgtgcactc ctaaagcgat gatgtctgcg aggggttctt cgttgaaccc    3660
tagttcaggc accatcttac cctcttattt tttcccgtgg gctttcattt tgtgtcatcc    3720
gagcatgacg ttgtagggtt ggagtttctt cctttttatc ttgtcattta ctggtaccca    3780
taggcgcgag actaggcttc catgttttgt tttgcgactt tcaaaaagta cttttagtgg    3840
tttggggcac gacgagggg ggcaacctct tctgtcgaaa aaggtggctg gatggatgag     3900
atgagatgag atgagggtga agatagatac ctgcagtgtt tttgacgcga cgggatggcg    3960
atcgc                                                                3965
```

<210> SEQ ID NO 5
<211> LENGTH: 20
<212> TYPE: DNA
<213> ORGANISM: Artificial
<220> FEATURE:
<223> OTHER INFORMATION: synthetic primer

<400> SEQUENCE: 5
ctgcgtgtgt cttctctagg                                                20

<210> SEQ ID NO 6
<211> LENGTH: 29
<212> TYPE: DNA
<213> ORGANISM: Artificial
<220> FEATURE:
<223> OTHER INFORMATION: synthetic primer

<400> SEQUENCE: 6
taggcgcgcc gctgactttg cctactagc                                      29

<210> SEQ ID NO 7
<211> LENGTH: 29
<212> TYPE: DNA
<213> ORGANISM: Artificial
<220> FEATURE:
<223> OTHER INFORMATION: synthetic primer

<400> SEQUENCE: 7
tagcgatcgc gtgagcccgt atcatgacg                                      29

<210> SEQ ID NO 8
<211> LENGTH: 20
<212> TYPE: DNA
<213> ORGANISM: Artificial
<220> FEATURE:
<223> OTHER INFORMATION: synthetic primer

<400> SEQUENCE: 8

```
gcatgttggc tggctcagtg                                                   20

<210> SEQ ID NO 9
<211> LENGTH: 22
<212> TYPE: DNA
<213> ORGANISM: Artificial
<220> FEATURE:
<223> OTHER INFORMATION: synthetic primer

<400> SEQUENCE: 9
gctaccatga ctgtcacgat ag                                                22

<210> SEQ ID NO 10
<211> LENGTH: 19
<212> TYPE: DNA
<213> ORGANISM: Artificial
<220> FEATURE:
<223> OTHER INFORMATION: synthetic primer

<400> SEQUENCE: 10
ggatggtggc gtgagcaag                                                    19

<210> SEQ ID NO 11
<211> LENGTH: 19
<212> TYPE: DNA
<213> ORGANISM: Artificial
<220> FEATURE:
<223> OTHER INFORMATION: synthetic primer

<400> SEQUENCE: 11
agagcttcca gtggtagtg                                                    19

<210> SEQ ID NO 12
<211> LENGTH: 19
<212> TYPE: DNA
<213> ORGANISM: Artificial
<220> FEATURE:
<223> OTHER INFORMATION: synthetic primer

<400> SEQUENCE: 12
cacgaccact ttgatctgc                                                    19

<210> SEQ ID NO 13
<211> LENGTH: 20
<212> TYPE: DNA
<213> ORGANISM: Artificial
<220> FEATURE:
<223> OTHER INFORMATION: synthetic primer

<400> SEQUENCE: 13
gtcaacacgt ctcctatgtc                                                   20

<210> SEQ ID NO 14
<211> LENGTH: 19
<212> TYPE: DNA
<213> ORGANISM: Artificial
<220> FEATURE:
<223> OTHER INFORMATION: synthetic primer

<400> SEQUENCE: 14
cggccctgca cgagttcct                                                    19

<210> SEQ ID NO 15
<211> LENGTH: 19
<212> TYPE: DNA
<213> ORGANISM: Artificial
<220> FEATURE:
```

```
<223> OTHER INFORMATION: synthetic primer

<400> SEQUENCE: 15
cacgaccact ttgatctgc                                                19

<210> SEQ ID NO 16
<211> LENGTH: 20
<212> TYPE: DNA
<213> ORGANISM: Artificial
<220> FEATURE:
<223> OTHER INFORMATION: synthetic primer

<400> SEQUENCE: 16
cacgagatga tgctgcgaca                                               20
```

METHOD FOR INTRODUCING NUCLEIC ACIDS INTO FUNGAL CELLS

FIELD

The method disclosed herein relates generally to introducing molecules such as biomolecules (e.g., nucleic acids) into a filamentous fungus. More specifically, the methods disclosed herein relate to introducing one or more nucleic acids into a filamentous fungus.

BACKGROUND

Filamentous fungi are useful systems for various functions and applications. Filamentous fungi, such as, for example, *Aspergillus* (e.g., *A. niger*) and *Trichoderma* (e.g., *T. reesei*) secrete a variety of cellulases and hemicellulases that hydrolyze plant-derived polysaccharides into sugar monomers which are then used as a carbon source and hence energy by the fungal cells. Accordingly, filamentous fungi are often ideal organisms for large scale industrial fermentation because of their ability to secrete fermentation products, such as, for example, heterologous proteins (e.g., swollenins, antibodies and enzymes, such as proteases, cellulases, glucoamylases, alpha amylases, xylanases, and phytases), into the culture media.

However, introduction of exogenous nucleic acids into filamentous fungus such as, for example, (i.e., transformation) has typically been a problem in constructing strains based in these hosts. Although methods for introducing exogenous nucleic acids into filamentous fungi are known (e.g., "biolistic" transformation and "protoplast-PEG" transformation) and reference is made to APPLIED MOLECULAR GENETICS OF FILAMENTOUS FUNGI, Ed., J R Kinghorn and G Turner, (1992) Chapter 1, May, G., "Fungal Technology", pgs 1-25, Blackie Academic & Professional, UK; Sanchez et al., (1996) Fungal Genetics Newsletter 43:48-51; ELECTROPORATION PROTOCOLS FOR MICROORGANISMS (1995) Ed. J A Nickoloff, Totowa, N.J. Humana Press; Cao et al., (2000) Protein Sci. 9:991-1001; Yelton et al., (1984) Proc. Natl. Acad. Sci. USA 81: 1470-1474; and Nevalainen et al., The Molecular Biology of *Trichoderma* and its Application to the Expression of Both Homologous and Heterologous Genes" in MOLECULAR INDUSTRIAL MYCOLOGY, Eds. Leong and Berka, Marcel Dekker Inc., NY (1992) pp 129-148, there is still a need for additional methods that introduce nucleic acids into filamentous fungi.

SUMMARY

The present invention is based, at least in part, on the discovery that foreign molecules, e.g., nucleic acids can be introduced into cells of filamentous fungi, especially fresh spores by applying an electric field to these cells.

In a first aspect, a method for introducing one or more nucleic acids into a filamentous fungus is provided. An electric field is applied to a mixture of the one or more nucleic acids and a fungal spore under conditions that allow intake of the nucleic acids by the fungal spore. In some embodiments, the fungal spore is a *Trichoderma* spore (e.g., *T. reesei* spore).

In a second aspect, a method for introducing one or more nucleic acids into a population of filamentous fungi is provided. An electric field is applied to a mixture of the one or more nucleic acids and a population of fungal spores under conditions that allow intake of the nucleic acids by the fungal spores. In some embodiments, the fungal spore is a *Trichoderma* spore (e.g., *T. reesei* spore).

Some aspects of the invention are methods for introducing one or more nucleic acids into filamentous fungal spores to produce transformed filamentous fungal spores, comprising mixing the spores with one or more nucleic acids and applying an electric field under conditions that allow introduction of the one or more nucleic acids into one or more fungal spores, wherein the electric field is applied at a voltage of between about 11,000 V/cm and about 20,000 V/cm to produce filamentous fungal spores. In some embodiments, the fungal spores are *Trichoderma* spores (e.g., *T. reesei*). In some embodiments, the mixture of nucleic acids is at a concentration of between about 100 µg/ml and about 0.05 mg/ml. In some embodiments, the one or more nucleic acids are mixed with the spores in a buffer and the ionic strength of the buffer is between about 0.0 mM and about 2.5 mM.

In some embodiments, the electric field is applied with a device and the capacitance of the device is between about 20 µF and about 100 µF and the resistance of the device is between about 40Ω and about 200Ω. In some embodiments, the electric field is applied at a voltage of between about 15,500 V/cm and about 18,500 V/cm. In some embodiments, the number of fungal spores having one or more nucleic acids introduced is between about 5 µg DNA and 400/µg DNA. In some embodiments, the method further comprises culturing the fungal spores after introduction of the nucleic acids. In some embodiments, the one or more nucleic acids comprise a gene of interest. In some embodiments, the gene of interest encodes a protein of interest. In some embodiments, the protein of interest is an endogenous or heterologous protein. In some embodiments, the protein of interest is a secreted protein. In some embodiments, the spores are collected before transformation by growing filamentous fungal cells in an appropriate medium for 5 to 15 days.

Further aspects of the invention are methods for introducing one or more nucleic acids into a population of filamentous fungal spores to produce transformed filamentous fungal spores, comprising contacting a population of filamentous fungal spores with one or more nucleic acids and applying an electric field under conditions that allow introduction of the nucleic acids into the fungal spores, wherein the electric field is applied at a voltage of between about 15,500 V/cm and about 18,500 V/cm to produce transformed filamentous fungal spores. In some embodiments, the fungal spores are *Trichoderma* spores (e.g., *T. reesei* spores). In some embodiments, the method further comprises culturing the fungal spores after application of the electric field. In some embodiments, the method further comprises growing fungal cells for 5 to 15 days under conditions in which they sporulate. In some embodiments, the electric field is applied with a device and the capacitance of the device is between about 20 µF and about 100 µF. In some embodiments, the electric field is applied with a device and the resistance of the device is between about 40Ω and about 200Ω.

Further aspects of the invention are methods for introducing one or more nucleic acids into a population of *Trichoderma* spores to produce transformed *Trichoderma* spores, comprising contacting a population of *Trichoderma* spores with one or more nucleic acids; and applying an electric field of between 15,500 V/cm and about 18,500 V/cm under conditions that allow introduction of the one or more nucleic acids into the fungal spores to produce transformed *Trichoderma* spores.

BRIEF DESCRIPTION OF THE DRAWINGS

FIGS. 5A-5B illustrate the als marker gene (SEQ ID NO: 4) used in example 4.

DETAILED DESCRIPTION

Figure 1A:
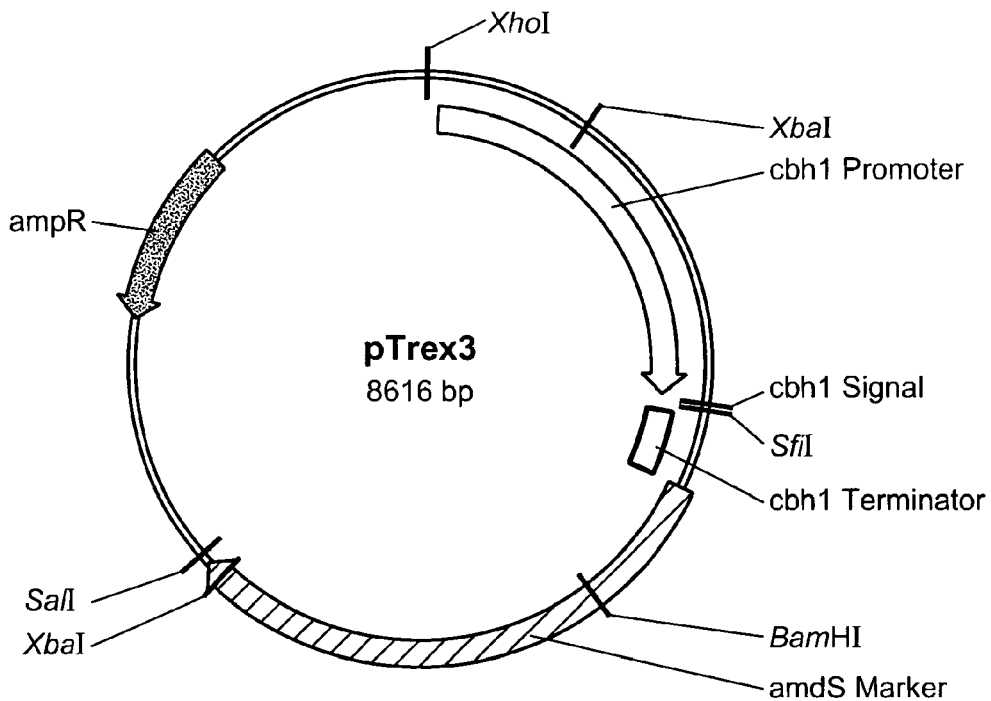
FIGS. 1A-1B illustrate the structure of the expression vector pTrex3g used to transform *Trichoderma reesei* spores as further described in example 1 (FIG. 1A) and example 2 (FIG. 1B).

Disclosed herein are methods of introducing one or more nucleic acids into a filamentous fungus. An electric field is applied to a mixture of the nucleic acids and a filamentous fungus spore in a condition which allows for intake of the nucleic acids by the filamentous fungus spore.

The invention will now be described in detail by way of reference only using the following definitions and examples. All patents and publications, including all sequences disclosed within such patents and publications, referred to herein are expressly incorporated by reference.

The practice of the present invention will employ, unless otherwise indicated, conventional techniques of cell biology, cell culture, molecular biology, transgenic biology, microbiology, recombinant DNA, and immunology, which are within the skill of the art. Such techniques are described in the literature. See, for example, *Molecular Cloning A Laboratory Manual*, 2nd Ed., ed. by Sambrook, Fritsch and Maniatis (Cold Spring Harbor Laboratory Press: 1989); Ausubel et al., Eds *Short Protocols in Molecular Biology* (5$^{th}$ Ed. 2002); *DNA Cloning*, Volumes I and II (D. N. Glover ed., 1985); *Oligonucleotide Synthesis* (M. J. Gait ed., 1984); Mullis et al. U.S. Pat. No. 4,683,195; *Nucleic Acid Hybridization* (B. D. Hames & S. J. Higgins eds. 1984); *Transcription And Translation* (B. D. Hames & S. J. Higgins eds. 1984); *Culture Of Animal Cells* (R. I. Freshney, Alan R. Liss, Inc., 1987); *Immobilized Cells And Enzymes* (IRL Press, 1986); B. Perbal, *A Practical Guide To Molecular Cloning* (1984); the treatise, *Methods In Enzymology* (Academic Press, Inc., N.Y.); *Gene Transfer Vectors For Mammalian Cells* (J. H. Miller and M. P. Calos eds., 1987, Cold Spring Harbor Laboratory); *Methods In Enzymology*, Vols. 154 and 155 (Wu et al. eds.), *Immunochemical Methods In Cell And Molecular Biology* (Mayer and Walker, eds., Academic Press, London, 1987); *Handbook Of Experimental Immunology*, Volumes I-IV (D. M. Weir and C. C. Blackwell, eds., 1986); *Manipulating the Mouse Embryo*, (Cold Spring Harbor Laboratory Press, Cold Spring Harbor, N.Y., 1986).

Other features and advantages of the invention will be apparent from the following detailed description, and from the claims. Although any methods and materials similar or equivalent to those described herein can be used in the practice or testing of the present invention, the preferred methods and materials are described.

Unless defined otherwise herein, all technical and scientific terms used herein have the same meaning as commonly understood by one of ordinary skill in the art to which this invention belongs. Singleton, et al., DICTIONARY OF MICROBIOLOGY AND MOLECULAR BIOLOGY, 2D ED., John Wiley and Sons, New York (1994), and Hale & Markham, THE HARPER COLLINS DICTIONARY OF BIOLOGY, Harper Perennial, N.Y. (1991) provide one of skill with general dictionaries of many of the terms used in this invention.

The headings provided herein are not limitations of the various aspects or embodiments of the invention which can be had by reference to the specification as a whole. Accordingly, the terms defined immediately below are more fully defined by reference to the specification as a whole. Numeric ranges are inclusive of the numbers defining the range. Unless otherwise indicated; nucleic acids are written left to right in 5' to 3' orientation; amino acid sequences are written left to right in amino to carboxy orientation, respectively.

It should be noted that, as used in this specification and the appended claims, the singular forms "a," "an," and "the" include plural references unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

Definitions

The terms "isolated" or "purified" refers to a protein that is altered from its natural state by virtue of separating the protein from one or more or all of the naturally occurring constituents with which it is associated in nature.

The terms "peptides", "proteins", and "polypeptides" are used interchangeably herein.

As used herein, "percent (%) sequence identity" with respect to the amino acid or nucleotides sequences identified is defined as the percentage of amino acid residues or nucleotides in a candidate sequence that are identical with the amino acid residues or nucleotides in a sequence of interest (e.g. a NSP24 signal peptide sequence), after aligning the sequences and introducing gaps, if necessary, to achieve the maximum percent sequence identity, and not considering any conservative substitutions as part of the sequence identity.

"Homologous", as used herein, refers to the sequence similarity between two polypeptide molecules or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared ×100. For example, if 6 of 10, of the positions in two sequences are matched or homologous then the two sequences are 60% homologous. By way of example, the DNA sequences ATTGCC and TATGGC share 50% homology. Generally, a comparison is made when two sequences are aligned to give maximum homology.

As used herein the term "vector" refers to a polynucleotide sequence designed to introduce nucleic acids into one or more cell types. Vectors include cloning vectors, expression vectors, shuttle vectors, plasmids, phage particles, cassettes and the like.

As used herein, "expression vector" means a DNA construct including a DNA sequence which is operably linked to a suitable control sequence capable of affecting the expression of the DNA in a suitable host.

The term "expression" means the process by which a polypeptide is produced based on the nucleic acid sequence of a gene.

As used herein, a substance (e.g. a polynucleotide or protein) "derived from" a microorganism means "isolated from" and means that the substance is native to the microorganism.

The term "filamentous fungi" refers to all filamentous forms of the subdivision Eumycotina (See, Alexopoulos, C. J. (1962), INTRODUCTORY MYCOLOGY, Wiley, New York and AINSWORTH AND BISBY DICTIONARY OF THE FUNGI, 9$^{th}$ Ed. (2001) Kirk et al., Eds., CAB International University Press, Cambridge UK). These fungi are characterized by a vegetative mycelium with a cell wall composed of chitin, cellulose, and other complex polysaccharides. The filamentous fungi of the present invention are morphologically, physiologically, and genetically distinct from yeasts. Vegetative growth by filamentous fungi is by hyphal elongation and carbon catabolism is obligatory aerobic.

As used herein, the term "spores" refers to any fungal propagating unit that serves in the production of new individuals.

As used herein, the term "*Trichoderma*" or "*Trichoderma* sp.*" refer to any fungal genus previously or currently classified as *Trichoderma*.

As used herein, the term "culturing" refers to growing a population of microbial cells under suitable conditions in a liquid or solid medium.

As used herein the term "contacting" refers to the placing of nucleic acids in sufficiently close proximity to the respective host to enable the nucleic acids to be taken up.

The term "introduced" in the context of inserting a nucleic acid sequence into a cell, means "transfection", or "transformation" or "transduction" and includes reference to the incorporation of a nucleic acid sequence into a eukaryotic or prokaryotic cell wherein the nucleic acid sequence may be incorporated into the genome of the cell (e.g., chromosome, plasmid, plastid, or mitochondrial DNA), converted into an autonomous replicon, or transiently expressed (e.g., transfected mRNA).

As used herein, the terms "transformed", "stably transformed" and "transgenic" used in reference to a cell means the cell has a non-native (e.g., heterologous) nucleic acid sequence integrated into its genome or as an episomal plasmid that is maintained through multiple generations. By "stably integrated" means that the episomal plasmic is maintained through multiple generations.

As used herein the term "heterologous" with reference to a polypeptide or polynucleotide means a polypeptide or polynucleotide that is not naturally expressed in a cell.

The term "homologous" or "endogenous" with reference to a polynucleotide or protein refers to a polynucleotide or protein that occurs naturally in the host cell.

As used herein a "protein of interest" is a heterologous protein or endogenous protein that is expressed heterologously.

As used herein, the term "expression" refers to the process by which a polypeptide is produced based on the nucleic acid sequence of a gene. The process includes both transcription and translation.

The term "selective marker" refers to a gene capable of expression in a host that allows for ease of selection of those hosts containing an introduced nucleic acid or vector. Examples of selectable markers include but are not limited to antimicrobials (e.g., hygromycin, bleomycin, or chloramphenicol) and/or genes that confer a metabolic advantage, such as a nutritional advantage on the host cell.

As used herein the term electric field refers to a region of space characterized by the existence of a force generated by electric charge.

As used herein the term capacitance refers is a measure of the amount of electric charge stored (or separated) for a given electric potential.

As used herein "electric potential" is the potential energy per unit of charge that is associated with a static electric field. It is typically measured in volts. The difference in electric potential between two points is known as voltage.

As used herein the term "resistance" or "electrical resistance" is a ratio of the degree to which an object opposes an electric current through it, measured as ohms ($\Omega$).

Description of the Invention

Filamentous fungus refers to all filamentous forms of the subdivision Eumycotina (Alexopuoulus, C. J. (1962), "Introductory Mycology," Wiley, New York and "Ainsworth and Bisby Dictionary of the Fungi," 9th Ed. (2001) Kirk et al., Eds., CAB International University Press, Cambridge UK). Filamentous fungi are characterized by a vegetative mycelium with a cell wall composed of chitin, cellulose and other complex polysaccharides and are morphologically, physiologically and genetically distinct from yeasts. Vegetative growth by filamentous fungi is by fungal elongation and carbon catabolism is obligatory aerobic. Filamentous fungi include, but are not limited to, *Aspergillus, Acremonium, Aureobasidium, Beauveria, Cephalosporium, Ceriporiopsis, Chaetomium Paecilomyces, Chrysosporium, Claviceps, Cochiobolus, Cryptococcus, Cyathus, Endothia, Fusarium, Giocladium, Humicola, Magnaporthe, Myceliophthora, Myrothecium, Mucor, Neurospora, Phanerochaete, Podospora, Paecilomyces, Penicillium, Pyricularia, Rhizomucor, Rhizopus, Schizophylum, Stagonospora, Talaromyces, Trichoderma, Thermomyces, Thermoascus, Thielavia, Tolypocladium, Trichophyton, Trametes* and *Pleurotus*. In some embodiments, the filamentous fungus is a *Trichoderma* fungus. In other embodiments, the filamentous fungi is *Trichoderma reesei* fungus. As used herein, the term "*Trichoderma*" or "*Trichoderma* sp.*" refer to any fungal genus previously or currently classified as *Trichoderma*.

In still other embodiments, the filamentous fungus is *A. nidulans, A. niger*, and *A. awomari*, e.g., NRRL 3112, ATCC 22342 (NRRL 3112), ATCC 44733, ATCC 14331 and strain UVK 143f; *A. oryzae*, e.g., ATCC 11490; *N. crassa*; *Trichoderma reesei*, e.g. NRRL 15709, ATCC 13631, 56764, 56765, 56466, and 56767; or *Trichoderma viride*, e.g., ATCC 32098 and 32086.

In general a fungal spore is a simple propagating unit that serves in the production of new individuals. The fungal spores used herein are typically intact and are collected from growth conditions which are known to one of skill in the art. In some embodiments, the fungi produce only one type of asexual spore, and in other embodiments, the fungi produces more than one type of asexual spore. In some embodiments, the spores are conidia spores. In some embodiments, the fungal spores only have one nucleus and in other embodiments the fungal spores are multi-nucleic.

In other embodiments, fungal spores are collected 4 days to 16 days after culturing. In some embodiments, the spores are collected about 7 days to 14 days after culturing. In some embodiments, the spores are collected 4-10 days after culturing. In some embodiments, the spores to be used in the method are freshly collected. Although one of general skill in the art will recognize that the culturing time and hence the collecting of spores may be longer or shorter than 4 to 16 days. While the spores may be in various stages of development when collected, the amount of germlings in the fungal spores is minimal and in some situations approximately zero. The collected spores will be essentially non-germinate.

In some embodiments, the collected spores are washed and then filtered by means known to those of general skill in the art.

Nucleic acids as used herein include DNA, RNA, single stranded or double stranded forms and circular or linear forms and chemical modifications thereof. In some embodiments, the nucleic acid concentration is between about 10 µg/ml and about 5.0 mg/ml. In other embodiments, the nucleic acid concentration is between about 10 µg/ml and about 0.5 mg/ml.

In still other embodiments, the nucleic acid concentration is between about 100 µg/ml and about 0.05 mg/ml.

In some embodiments, the mixture of nucleic acids and the fungal spores are suspended in an aqueous buffer. Numerous buffers are known in the art and selection of an appropriate buffer is well within the knowledge of those of skill in the art. In some embodiments the buffer does not contain lithium acetate.

In some embodiments, the ionic strength of the buffer is between about 0.0 mM and about 2.5 mM. In other embodiments, the ionic strength of the buffer is between about 0.0 mM and about 2.00 mM. In still other embodiments, the ionic strength of the buffer is between about 0.1 mM and about 2.00 mM. In still other embodiments, the ionic strength of the buffer is between about 0.5 mM and about 2.00 mM. In still other embodiments, the ionic strength of the buffer is between about 0.25 mM and about 1.75 mM. In still other embodiments, the ionic strength of the buffer is between about 0.50 mM and about 1.50 mM. In still other embodiments, the ionic strength of the buffer is between about 0.75 mM and about 1.25 mM.

While not wishing to be bound by theory, application of an electric field to fungal spores typically leads to significant increase in the electrical conductivity and permeability of the fungal spore membrane. In certain circumstances, pores may be formed in the spore membrane upon application of an electric field which may allow for introduction of foreign molecules such as nucleic acids. Typically, pores are formed when the voltage of the applied electric field exceeds its dielectric strength and under ideal circumstances may reseal.

In some embodiments, the voltage (V) of the electric field is between about 11,000 V/cm and about 20,000 V/cm. In other embodiments, the voltage of the electric field is between about 12,000 V/cm and about 20,000 V/cm. In still other embodiments, the voltage of the electric field is between about 14,000 V/cm and about 19,000 V/cm. In still other embodiments, the voltage of the electric field is between about 15,500 V/cm and about 18,500 V/cm. In still other embodiments, the voltage of the electric field is between about 16,000 V/cm and about 18,000 V/cm. In still other embodiments, the voltage of the electric field is at least about 18,000 V/cm. In still other embodiments, the voltage of the electric field is at least about 16,000 V/cm. However, it is understood that the voltage may vary depending upon the capacitance and other parameters. One of skill in the art would know how to vary the voltage taking into account these parameters.

In some embodiments, the electric field is applied with a device. The device typically includes a pair of electrodes, a capacitor and a resistor. In some embodiments, the electric field is applied with an electroporator. Electroporators are well known in the art and may be purchased from commercial vendors such as, for example, BioRad, Hercules, Calif. (GenePulser II).

In some embodiments, the capacitance (µF) of the device is between about 20 µF. and about 100 µF. In other embodiments, the capacitance of the device is between about 20 µF and about 50 µF. In other embodiments, the capacitance of the device is between about 25 µF and about 30 µF. In other embodiments, the capacitance of the device is at least about 25 µF. In some of the above embodiments, the device is an electroporator.

In some embodiments, the resistance (Ω=ohms) of the device is between about 40Ω and 200Ω. In other embodiments, the resistance of the device is between about 40Ω and 100Ω. In some embodiments, the resistance of the device is between about 45Ω and 65Ω. In other embodiments, the resistance of the device is at least about 50Ω. In some of the above embodiments, the device is an electroporator.

In some embodiments, the voltage of the device is between about 15,500 V/cm and about 18,500 V/cm and the capacitance of the device is about 25 µF. In other embodiments, the voltage of the device is between about 15,500 V/cm and about 18,500 V/cm and the resistance of the device is about 50Ω. In still other embodiments, the capacitance of the device is about 25 µF and the resistance of the device is about 50Ω. In some of the above embodiments, the device is an electroporator.

In some embodiments, the voltage of the device is between about 15,500 V/cm and about 18,500 V/cm, the capacitance of the device is about 25 µF and the resistance of the device is about 50Ω. In other embodiments, the voltage of the device is about 16,000 V/cm, the capacitance of the device is about 25 µF and the resistance of the device is about 50Ω. In some of the above embodiments, the device is an electroporator.

Also provided herein are methods for introducing one or more nucleic acids into a population of filamentous fungi. An electric field is applied to a mixture of the one or more nucleic acids and a population of fungal spores under conditions that allow intake of the nucleic acids by the fungal spores. Typically the above method will provide a population of stable transformed filamentous fungus spores. The percentage of stable transformants will typically be between about 5% and about 100% of the fungal spore population. In some embodiments, the percentage of stable transformants will typically be between about 10% and about 100% of the fungal spore population. In other embodiments, the percentage of stable transformants will typically be greater than 25% of the fungal spore population. The term transformed is used herein to mean a cell (e.g., a spore) having an introduced nucleic acid sequence integrated into its genome or as an episomal plasmid that is maintained through multiple generations by the method encompassed by the invention described herein. In some embodiments, the electroporation method is not a lithium acetate method. Thus, the method is performed without the use of lithium acetate, beta glucuronidase or other cell wall modifying substances.

In some embodiments, the number of transformants in a population will be between about 400 transformants/µg DNA and about 5 transformants/µg DNA; also about 250 transformants/µg DNA and about 5 transformants/µg DNA and also between 200 transformants/µg DNA and about 10 transformants/µg DNA. In some embodiments, the number of transformants will be at least 150 transformants/µg DNA; also at least 100 transformants/µg DNA and also at least 50 transformants/µg DNA. Preferably, the methods of transformation of the present invention results in the stable integration of all or part of the expression vector comprising the nucleic acid coding for a desired protein into the genome of the filamentous fungus.

In some embodiments, the method includes inoculating buffer medium with fungal spores from *Trichoderma* (e.g., *T.*

*reesei*), growing the spores at about between 28° C. and 32° C. (e.g., 30° C.), for 5 days to about 15 days, mixing the spores with an expression vector comprising DNA to obtain a suspension, applying an electric field between about 15,500 V/cm to about 18,500 V/cm to the suspension, incubating the spores at 0 to about 4° C. for about 15 min to 60 min to obtain a transformation mixture, culturing the transformation mixture under suitable transformation conditions.

In some embodiments, the transformants observed from the cultures are recovered. In some embodiments, the transformed cells are further cultured under culturing conditions favoring expression of genes introduced into the transformants. Large batches of transformed cells can be cultured by methods well known in the art and, in some embodiments, the expression product is recovered from the culture using standard techniques.

Thus, the invention herein provides for the expression and in some embodiments, secretion of desired polypeptides whose expression is under control of gene promoter sequences. Optimal conditions for the production of the proteins will vary with the choice of the host cell, and with the choice of protein to be expressed. Such conditions will be easily ascertained by one skilled in the art through routine experimentation or optimization.

In some embodiments, the desired protein that is produced in the transformed cell by a method according to the invention will be an enzyme, e.g., a so-called "industrial enzyme", or a protein having therapeutic activity, such an antibody. The protein produced from a transformed cell may be a homologous or a heterologous protein of the cell.

In particular embodiments, therefore, the fungal cell may be transformed with a vector comprising a nucleic acid that encodes for a carbohydrase, such as an α-amylase, a β-amylase, a cellulase; a dextranase, an α-glucosidase, an α-galactosidase, a glucoamylase, a hemicellulase, a pentosanase, a xylanase, an invertase, a lactase, a naringanase, a pectinase or a pullulanase; a protease such as an acid protease, an alkali protease, a neutral protease, papain, pepsin, a peptidase, rennet, rennin, chymosin, subtilisin, thermolysin, an aspartic proteinase, or trypsin; a lipase or esterase, such as a triglyceridase, a phospholipase, a pregastric esterase, a phosphatase, a phytase, an amidase, an iminoacylase, a glutaminase, a lysozyme, or a penicillin acylase; an isomerase such as glucose isomerase; an oxidoreductases, e.g., an amino acid oxidase, a catalase, a chloroperoxidase, a glucose oxidase, a hydroxysteroid dehydrogenase or a peroxidase; a lyase such as a acetolactate decarboxylase, an aspartic β-decarboxylase, a fumarese or a histadase; a transferase such as cyclodextrin glycosyltranferase; or a ligase, for example.

In other embodiments, the protein may be a therapeutic protein such as a glycosylated therapeutic protein (i.e., a protein having a therapeutic biological activity that would be glycosylated in an equivalent cell, e.g., an equivalent cell not altered by the methods described above). Examples of suitable target glycoproteins which may be produced using a subject cell include: erythropoietin, cytokines such as interferon-α, interferon-β, interferon-γ, interferon-ο, and granulocyte-CSF, GM-CSF, coagulation factors such as factor VIII, factor IX, and human protein C, antithrombin III, thrombin, soluble IgE receptor α-chain, IgG, IgG fragments, IgG fusions, IgM, IgA, interleukins, urokinase, chymase, and urea trypsin inhibitor, IGF-binding protein, epidermal growth factor, growth hormone-releasing factor, annexin V fusion protein, angiostatin, vascular endothelial growth factor-2, myeloid progenitor inhibitory factor-1, osteoprotegerin, .alpha.-1-antitrypsin, α-feto proteins, DNase II, kringle 3 of human plasminogen, glucocerebrosidase, TNF binding protein 1, follicle stimulating hormone, cytotoxic T lymphocyte associated antigen 4-Ig, transmembrane activator and calcium modulator and cyclophilin ligand, soluble TNF receptor Fc fusion, glucagon like protein 1 and IL-2 receptor agonist. Monoclonal antibodies are of particular interest.

A desired protein or protein of interest encoded by a nucleic acid introduced into a fungus (e.g., spores of a *Trichoderma* sp.) may be a heterologous or an endogenous protein. A heterologous protein means a polypeptide or protein that does not naturally occur in a host. An endogenous protein means a polypetide or protein that may occur naturally in the host cell but is introduced according to the method encompassed by the invention into the host. An endogenous polypeptide coded for by a nucleic acid introduced into the cell by a method encompassed by the invention may be overexpressed in the host.

In some embodiments, the protein produced by the transformed cell may be secreted from the cell into culture media.

The protein of interest may be isolated or purified in a variety of ways known to those skilled in the art depending on what other components are present in the sample. Standard purification methods include electrophoretic, molecular, immunological and chromatographic techniques, including ion exchange, hydrophobic, affinity, and reverse-phase HPLC chromatography, and chromatofocusing. For example, the protein of interest may be purified using a standard antiprotein of interest antibody column. Ultrafiltration and diafiltration techniques, in conjunction with protein concentration, are also useful.

In some embodiments, the invention provides for the expression of exogenous genes (heterologous genes or homologous genes) under control of the gene promoters functional in *Trichoderma reesei*. Therefore, this invention relies on routine techniques in the field of recombinant genetics. Basic texts disclosing the general methods of use in this invention include Sambrook et al., MOLECULAR CLONING, A LABORATORY MANUAL (2nd ed. 1989); Kriegler, GENE TRANSFER AND EXPRESSION: A LABORATORY MANUAL (1990); and Ausubel et al., eds., CURRENT PROTOCOLS IN MOLECULAR BIOLOGY (1994)).

Exogenous genes comprising gene promoter sequences of filamentous fungi are frequently cloned into intermediate vectors before transformation into *Trichoderma reesei* cells for replication and/or expression. These intermediate vectors are typically prokaryotic vectors, e.g., plasmids, or shuttle vectors. Examples of suitable expression and/or integration vectors are provided in Sambrook et al., (1989) supra, and Ausubel (1987) supra, and van den Hondel et al. (1991) in Bennett and Lasure (Eds.) MORE GENE MANIPULATIONS IN FUNGI, Academic Press pp. 396-428 and U.S. Pat. No. 5,874,276. Reference is also made to the Fungal Genetics Stock Center Catalogue of Strains (FGSC, <www.fgsc.net>) for a list of vectors. Particularly useful vectors include vectors obtained from for examples Invitrogen and Promega.

To obtain high level expression of a cloned gene, the heterologous gene is preferably positioned about the same distance from the promoter as is in the naturally occurring gene. As is known in the art, however, some variation in this distance can be accommodated without loss of promoter function.

Those skilled in the art are aware that a natural promoter can be modified by replacement, substitution, addition or elimination of one or more nucleotides without changing its function. The practice of the invention encompasses and is not constrained by such alterations to the promoter. The nucleic acid sequence coding for a polypeptide may be operably linked to promoter, a signal sequence, and optionally other regulatory nucleic acid sequences.

A suitable promoter may be derived from genes encoding proteins either homologous or heterologous to the host cell. The promoter may be a truncated or hybrid promoter. Further the promoter may be an inducible or constitutive promoter. Preferably the promoter is useful in *Aspergillus* or *Trichoderma* cells. Suitable nonlimiting examples of promoters include cbh1, cbh2, egl1, pepA, hfb1, hfb2, xyn1 and amy. In some embodiments, the promoter will be a *Trichoderma reesei* cbh1 promoter. The *T. reesei* cbh1 is an inducible promoter and has been deposited in GenBank under Accession No. D86235. In other embodiments, the promoter will be derived from the genes encoding an *Aspergillus awamori* or *Aspergillus niger* glucoamylase (glaA) (Nunberg et al., (1984) Mol. Cell Biol. 4:2306-2315 and Boel et al., (1984) EMBO J. 3:1581-1585), an *Aspergillus niger* alpha amylase, an *Aspergillus oryzae* TAKA amylase or a *Rhizomucor miehei* aspartic proteinase.

In some embodiments, a vector to be transformed into a host cell which comprises a nucleic acid encoding a desired protein will further include a selectable marker. Examples of selectable markers include but are not limited to ones that confer antimicrobial resistance (e.g. hygromycin, bleomycin, chloroamphenicol and phleomycin). Genes that confer metabolic advantage, such as nutritional selective markers also find use in the invention. Some of these markers include amdS, argB and pyr4. Reference is made to Kelley et al., (1985) EMBO J. 4: 475-479; Penttila et al., (1987) Gene 61:155-164 and Kinghorn et al (1992) Applied Molecular Genetics of Filamentous Fungi, Blackie Academic and Professional, Chapman and Hall, London.

An expression vector/construct typically contains a transcription unit or expression cassette that contains all the additional elements required for the expression of an exogenous sequence. A typical expression cassette thus contains a promoter operably linked to the heterologous nucleic acid sequence and signals required for efficient polyadenylation of the transcript, ribosome binding sites, and translation termination. Additional elements of the cassette may include enhancers and, if genomic DNA is used as the structural gene, introns with functional splice donor and acceptor sites. In some embodiments, the vector that is used to transform the cells will be linearized.

The expression cassette generally should also contain a transcription termination region downstream of the structural gene to provide for efficient termination. The termination region may be obtained from the same gene as the promoter sequence or may be obtained from different genes.

Although any fungal terminator is likely to be functional in the present invention, preferred terminators include: the terminator from *Aspergillus nidulans* trpC gene (Yelton, M. et al. (1984) PNAS USA 81:1470-1474, Mullaney, E. J. et al. (1985) MGG 199:37-45), the *Aspergillus awamori* or *Aspergillus niger* glucoamylase genes (Nunberg, J. H. et al. (1984) Mol. Cell. Biol. 4:2306, Boel, E. et al.(1984) EMBO J. 3:1581-1585) and the *Mucor miehei* carboxyl protease gene (EPO Publication No. 0 215 594).

The particular expression vector used to transport the genetic information into the cell is not particularly critical. Any of the conventional vectors used for expression in eukaryotic may be used. The elements that are typically included in expression vectors also include a gene encoding a selective marker (e.g. an antibiotic resistance gene) to permit selection of transformants that harbor recombinant plasmids, and unique restriction sites in nonessential regions of the plasmid to allow insertion of heterologous sequences. The prokaryotic sequences are preferably chosen such that they do not interfere with the replication or integration of the DNA in *Trichoderma reesei*.

In one embodiment, the vector pTrex3g (FIG. 1A) is used for transformation by a method according to the invention. This vector is based on the *E. coli* vector pSL1180 (Pharmacia Inc., Piscataway, N.J.) which is a pUC118 phagemid based vector (Brosius, J. (1989), *DNA* 8:759) with an extended multiple cloning site containing 64 hexamer restriction enzyme recognition sequences. The vector is designed as a Gateway destination vector (Hartley et al., (2000) *Genome Research* 10:1788-1795) to allow insertion using Gateway technology (Invitrogen) of any desired open reading frame between the promoter and terminator regions of the *T. reesei* cbh1 gene. It also contains the *Aspergillus nidulans* amdS gene for use as a selective marker in the electroporation transformation method of the invention. However, as mentioned above the electroporation method encompassed by the invention is not limited by the type of vector.

Transformed cells can be cultured in conventional nutrient media. The culture media for transformed cells may be modified as appropriate for activating promoters and selecting transformants. The specific culture conditions, such as temperature, pH and the like, may be those that are used for the host cell selected for expression, and will be apparent to those skilled in the art. In addition, preferred culture conditions may be found in the scientific literature such as Sambrook, (1982) supra; Kieser, T, M J. Bibb, M J. Buttner, K F Chater, and D. A. Hopwood (2000) PRACTICAL STREPTOMYCES GENETICS. John Innes Foundation, Norwich UK; Harwood, et al., (1990) MOLECULAR BIOLOGICAL METHODS FOR BACILLUS, John Wiley and/or from the American Type Culture Collection (ATCC; www.atcc.org). Stable transformants of fungal host cells, such as *Trichoderma* cells can generally be distinguished from unstable transformants by their faster growth rate or the formation of circular colonies with a smooth rather than ragged outline on solid culture medium.

Integration of a vector introduced into a fungal cell according to the method encompassed by the invention may be homologous or non-homologous. In some embodiments, the vector is one that includes a nucleic acid coding for an enzyme, such as a glucoamylase, alpha amylase, phytase, protease, or cellulase wherein the vector is integrated into the cell by homologous integration. Homologous recombination means the exchange of DNA fragments between two DNA molecules or paired chromosomes at the site of identical or nearly identical nucleotide sequences. In a preferred embodiment, chromosomal integration is by homologous recombination. The methods of transformation of the present invention may result in the stable integration of all or part of the vector into the genome of a filamentous fungus.

Experimental

The invention is further defined by reference to the following examples, which describe in detail, preparation of compounds of the invention and methods for assaying for biological activity. It will be apparent to those skilled in the art that many modifications, both to materials and methods, may be practiced without departing from the scope of the invention.

In the experimental disclosure which follows, the following abbreviations apply: M (Molar); µM (micromolar); N (Normal); mol (moles); mmol (millimoles); µmol (micromoles); nmol (nanomoles); g (grams); mg (milligrams); kg (kilograms); µg (micrograms); L (liters); ml (milliliters); µl (microliters); cm (centimeters); mm (millimeters); µm (micrometers); nm (nanometers); PCR (polymerase chain reaction); ° C. (degrees Centigrade); h (hours); min (minutes); sec (seconds); msec (milliseconds); ORF (open reading frame); and V (voltage).

EXAMPLES

Example 1

Electroporation Efficiency of *Trichoderma reesei* Spores as a Function of Electroporation Voltage A *T. reesei* strain derived from RL-P37 (IA52) was grown and sporulated on Potato Dextrose Agar plates (Difco) for about 10-20 days. The spores were washed from the surface of the plates with water and purified by filtration through Miracloth (Calbiochem). The spores were collected by centrifugation (3000×G, 12 min), washed once with ice-cold water and once with ice-cold 1.1M sorbitol. The spore pellet was re-suspended in a small volume of cold 1.1 M sorbitol, mixed with about 8 µg of XbaI hydrolysate of pTrex3 (FIG. 1) per 100 µl of spore suspension. The mixture (100 µl) was placed into an electroporation cuvette (1 mm gap) and subjected to an electric pulse using the following electroporation parameters: voltage 6000-20000 V/cm, capacitance=25 µF, resistance=50Ω. After electroporation, the spores were diluted about 100-fold into 5:1 mixture of 1.1 M sorbitol and YEPD (1% yeast extract, 2% Bacto-peptone, 2% glucose, pH 5.5), placed in shake flasks and incubated for 16-18 hours in an orbital shaker (28° C. and 200 rpm). The spores were once again collected by centrifugation, re-suspended in about 10-fold of pellet volume of 1.1 M sorbitol and plated onto two 15 cm Petri plates containing amdS modified medium (acetamide 0.6 g/l, cesium chloride 1.68 g/l, glucose 20 g/l, potassium dihydrogen phosphate 15 g/l, magnesium sulfate heptahydrate 0.6 g/l, calcium chloride dihydrate 0.6 g/l, iron (II) sulfate 5 mg/l, zinc sulfate 1.4 mg/l, cobalt (II) chloride 1 mg/l, manganese (II) sulfate 1.6 mg/l, agar 20 g/l and pH 4.25). Transformants appeared until about 1 week of incubation. Counting of colonies at this stage was difficult because of overgrowths of early transformants. Therefore, numerical estimates were made by counting transformants after 4 days of incubation. FIG. 2 illustrates data depicting the optimal voltage for transformation of *T. reesei* spores which is about 18000 V/cm. However, at this high voltage "arcing" in the electroporation cuvette is often a problem. The use of 16 000V/cm significantly reduced arcing yet retained acceptable transformation efficiency. Transformants were not obtained using the voltage range of 6000-8000V/cm.

Example 2

Transformation of a Recombinant *Trichoderma reesei* Strain with a Phytase Expression Cassette A recombinant *T. reesei* strain was used for transformation by the electroporation method of the invention. The expression vector used to transform the recombinant *T. reesei* strain included the coding sequence for a polypeptide having phytase activity. The phytase is designated BP17 and was derived from a wild-type phytase from *Buttiauxella* sp (Miaskinov et al., International Publication No. WO 2006/043178).

The amino acid sequence of the mature protein of BP-17 is as follows:

```
                                            (SEQ ID NO: 1)
NDTPASGYQV EKVVILSRHG VRAPTKMTQT MRDVTPNTWP

EWPVKLGYIT PRGEHLISLM GGFYRQKFQQ QGILSQGSCP

TPNSIYVWTD VAQRTLKTGE AFLAGLAPQC GLTIHHQQNL

EKADPLFHPV KAGICSMDKT QVQQAVEKEA QTPIDNLNQH

YIPSLALMNT TLNFSKSPWC QKHSADKSCD LGLSMPSKLS

IKDNGNEVSL DGAIGLSSTL AEIFLLEYAQ GMPQAAWGNI

HSEQEWALLL KLHNVYFDLM ERTPYIARHK GTPLLQAISN

ALNPNATESK LPDISPDNKI LFIAGHDTNI ANIAGMLNMR

WTLPGQPDNT PPGGALVFER LADKSGKQYV SVSMVYQTLE

QLRSQTPLSL NQPAGSVQLK IPGCNDQTAE GYCPLSTFTR

VVSQSVEPGC QLQ
```

Figure 1B:
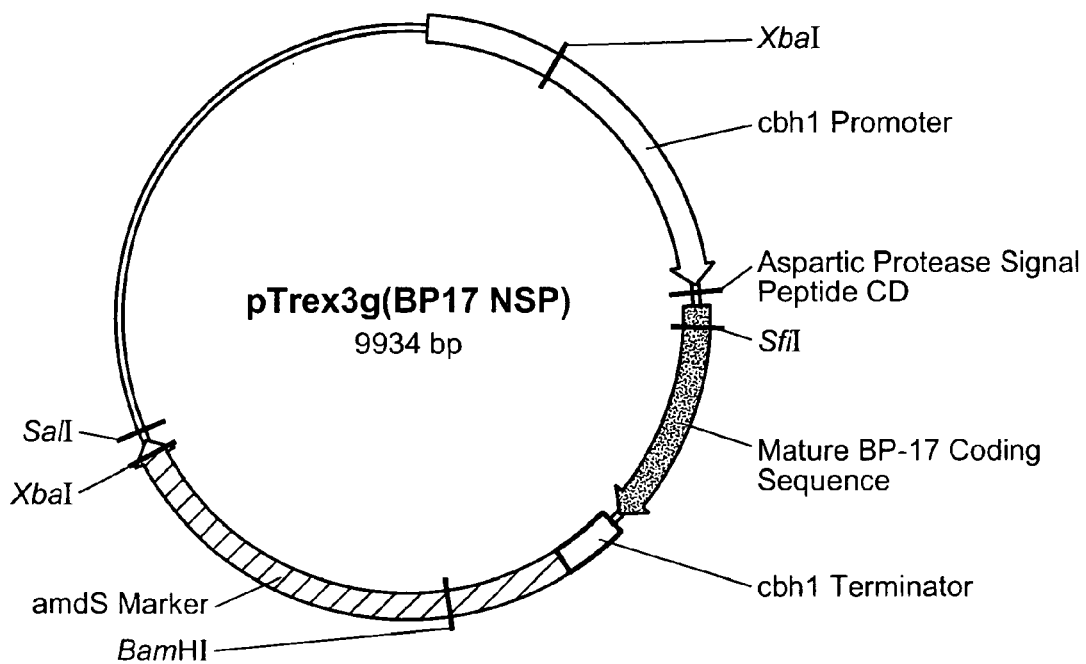
Figure 2:
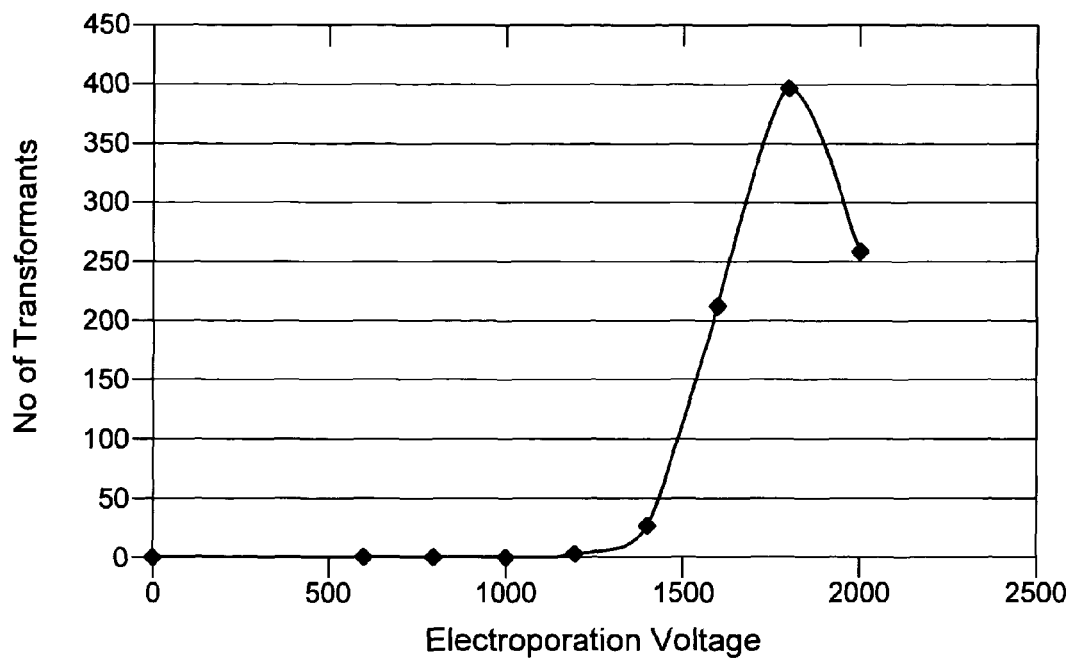
FIG. 2 illustrates the electroporation efficiency of *T. reesei* spores as a function of voltage.

The BP-17 coding sequence was fused to an aspartic protease signal peptide MQTFGAFLVSFLAASGLAAA (SEQ ID NO: 2) having a nucleic acid sequence of ATGCAGAC-CTTTGGAGCTTTTCTCGTTTCCTTC-CTCGCCGCCAGCGGCCTGGCCGCG GCC, (SEQ ID NO:3) and placed under the control of *T. reesei* cbhI promoter and transcription terminator in expression vector pTrex3g to obtain the vector illustrated in FIG. 1B. A 5.85 kb XbaI-XbaI fragment of pTrex3g comprising the expression cassette and a selectable marker (amdS gene from *Aspergillus nidulans*) was purified by agarose gel electrophoresis and used to transform the recombinant *T. reesei* strain by the procedure described in Example 1 using 16 kV/cm voltage. Transformant colonies appeared in a period between 4 days to about 1 week after plating. Individual transformants were transferred onto fresh acetamide selective plates and grown for 3-4 days. Most isolates showed stable growth on selective medium. The clones (38) were used to inoculate 5 ml of lactose defined medium (Foreman et al., International Publication No. WO 2005/001036) in 20×175 mm test tubes. The tubes were fixed in a rotary shaker at about 45° angle and shaken at 200 rpm and 28° C. for 4-5 days.

Example 3

Analysis of Phytase Gene Expression in *T. reesei* Transformants

Figure 3:
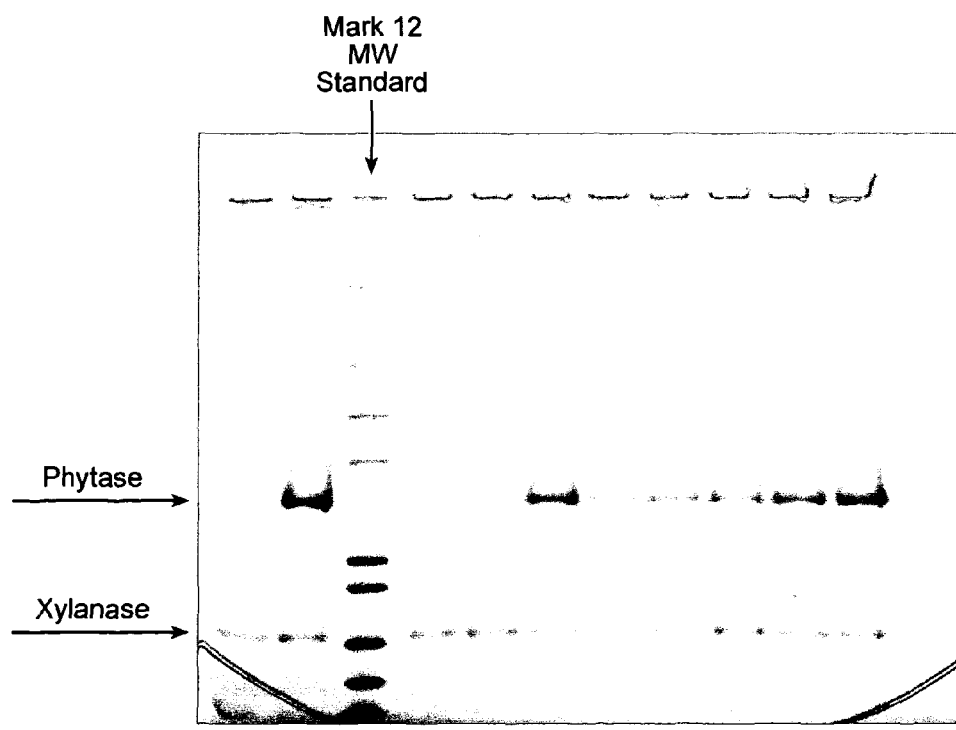
FIG. 3 illustrates SDS PAGE analysis of 10 clones from a set of *Trichoderma reesei* transformants with an expression cassette having a polynucleotide that codes for a polypeptide having phytase activity.

The culture medium of the transformants obtained and cultivated as described in example 2 was separated from mycelium by centrifugation (16000×G, 10 min) and analyzed by acrylamide gel electrophoresis in the presence of sodium dodecyl sulfate (SDS PAGE). The results of a typical experiment are shown in FIG. 3. About ⅔ of all studied transformants (24 out of 38) expressed the phytase gene at levels easily detectable by SDS PAGE. The expression levels of phytase varied largely between clones. Phytase assays were carried out using as a substrate 7.5 mM phytase in 100 mM sodium acetate buffer, containing 1 mg/ml BSA at a final pH 5.0. The culture supernatants (20 µl, diluted 1:80 and 1:160), were mixed with 100 µl of the substrate solution and incubated for 90 min at 25° C. The reaction was quenched by addition of 100 µl of a freshly made solution containing 1 part of 10% ammonium molybdate, 1 part of 0.24% ammonium vanadate and 2 parts of 20% nitric acid. After centrifugation (16000×G for 10 min), 200 µl of supernatant from each reaction was transferred into a well of a microtitre plate and the absorbance at 405 nm was recorded. The difference in absorbance between the experimental and control samples (containing water instead of the enzyme solution) was taken as the measure of enzymatic activity. The results of the determination of phytase activity in 8 different clones are summarized in Table 1.

TABLE 1

Phytase activity in a representative set of transformants

| Clone number | Phytase activity, Arbitrary units |
|---|---|
| 5 | 0.27 |
| 10 | 1.21 |
| 22 | 0.31 |
| 25 | 0.53 |
| 26 | 0.17 |
| 27 | 0.23 |
| 31 | 0.23 |
| 32 | 0.72 |

Example 4

Deletion of cbh1 Gene from a *Trichoderma reesei* Strain

Construction of Deletion Cassette—

Figure 4A:
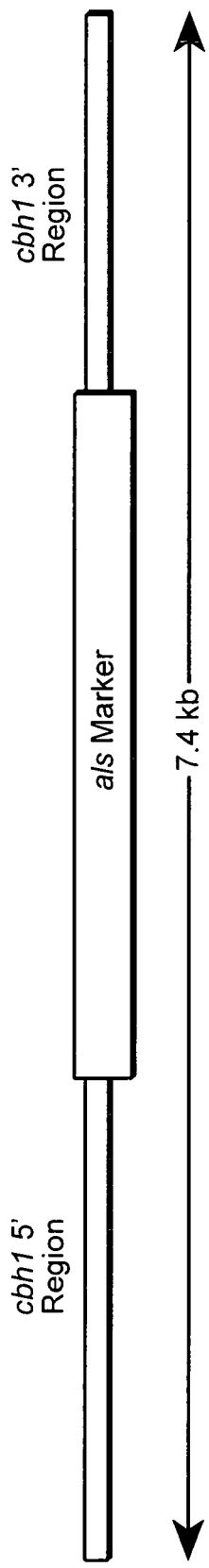
FIGS. 4A-4B depict the deletion vector used in example 4.
Figure 4B:
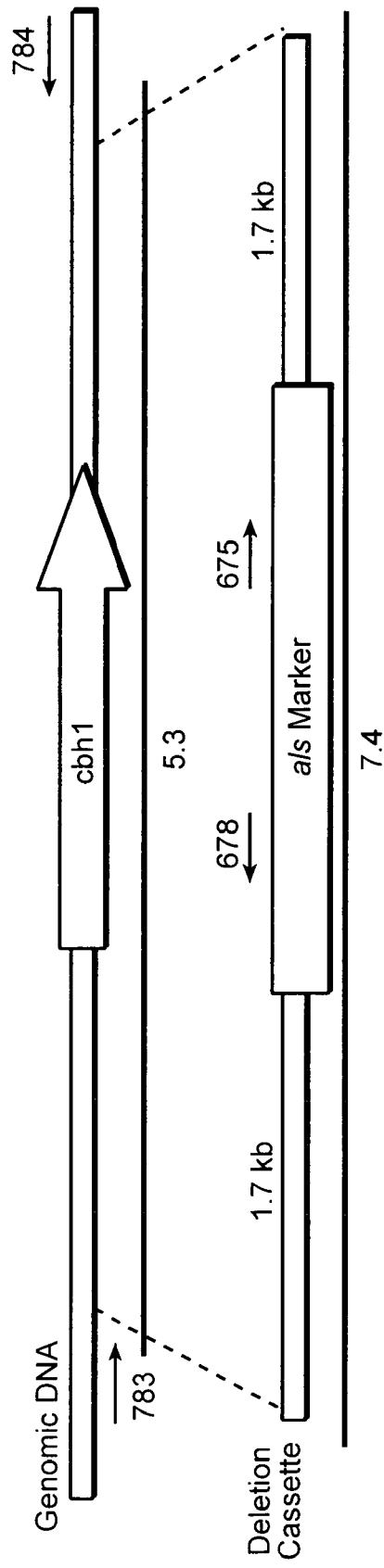

The native cbh1 gene from a *Trichoderma reesei* strain was performed using the electroporation transformation method encompassed by the invention. The deletion cassette used in the experiment consisted of the acetyl lactate synthases (als) marker gene as depicted in FIG. 5 (SEQ ID NO: 4) flanked by the 5' and 3' native cbh1 sequence. The 5' upstream and 3' downstream sequences of the native cbh1 gene were amplified by PCR using purified genomic DNA from *Trichoderma reesei* strain RL-P37 as the template. The native *Trichoderma reesei* als gene marker was digested from a pre-existing plasmid using AscI and AsiSI sites (New England BioLabs restriction enzymes). The PCR machine used for the reactions was a Peltier Thermal Cycler PTC-200 (MJ Research). The DNA polymerase used was Pfu Ultra II (Stratagene). The primers used for amplifying the 5' upstream cbh1 sequence (approx. 1.7 kb) for the deletion vector were SK775 (forward) 5'-CTGCGTGTGTCTTCTCTAGG-3' (SEQ ID NO: 5), and SK776 (reverse) 5'-TAGGCGCGCCGCTGACTTTGC-CTACTAGC-3'(SEQ ID NO: 6). The primers used for amplifying the 3' downstream cbh1 sequence (approx. 1.7 kb) for the deletion vector were SK777 (forward) 5'-TAGC-GATCGCGTGAGCCCGTATCATGACG-3' (SEQ ID NO:7), and SK778 (reverse) 5'-GCATGTTGGCTGGCT-CAGTG-3' (SEQ ID NO:8). For primers SK776 and SK777, an AscI and an AsiSI site were incorporated respectively at the 5' ends for subsequent cloning of the als marker between the 5' and the 3' cbh1 sequences. In addition primer SK777 was phosphorylated at the 5' end for subsequent ligation reaction of the PCR fragments obtained of the 5' and 3' regions of the native cbh1 gene. The PCR products of SK775 vs. SK776 and SK777 vs. 778 were ligated using T4 ligase (Roche). The ligation mixture was incubated at room temperature for 15 min. Fusion PCR was performed on the ligated 5' (SK775 vs. SK776) and 3' (SK777 vs. SK778) PCR products using primers SK775 and SK778. The resulting SK775 vs. SK778 fusion PCR product was cloned into TOPO Blunt II vector (Invitrogen). An AscI site in the cloned fusion PCR product of SK775 vs. SK778 was eliminated using Quikchange Site-Directed Mutagenesis (Stratagene) with primers SK790 (forward) and SK791 (reverse). The als marker gene fragment (approx. 3950 bp) was cloned into the resulting TOPO Blunt II vector from the site-directed mutagenesis PCR reaction, between the 5' and 3' cbh1 sequences at the AscI and AsiSI sites. This resulted in a vector with the final deletion cassette (approx. 7.4 kb) (FIG. 4).

Electroporation of Spores—

The deletion cassette was re-amplified to obtained enough DNA for electroporation, with either primer pairs SK775 and SK778, or SK775 and SK817 (reverse) 5'-GCTACCAT-GACTGTCACGATAG-3' (SEQ ID NO: 9). PCR conditions for amplifying the deletion cassette to use for fungal transformation were as follows: Step 1: 94° C. for 1 min. and 30 sec. Step 2: 94° C. for 30 sec. Step 3: 56° C. for 30 sec. Step 4: 72° C. for 2 min. and 30 sec. Steps 2, 3 and 4 were repeated for an additional 28 cycles. Step 5: 72° C. 2 min. Both type of PCR products were purified using the QIAquick PCR Purification Kit (Qiagen), and concentrated before using in the electroporation. The electroporation apparatus used for the experiment was Gene Pulser Xcell System (Biorad). Spores of the *Trichoderma reesei* strain were resuspended from PDA plates with 1.1 M sorbitol, and filtered through sterile Miracloth. The spores were washed twice with 1.1 M sorbitol, and resuspended to a final concentration of $1\times10^8$ for electroporation. Approximately 10 ug of DNA was added to 100 ul of spores placed on ice. The spores were then transferred to 0.1 cm electroporation cuvetttes on ice. The electroporation was carried out at 16 kV/cm, 25 uF, 50Ω. The electroporated spores were immediately transferred to 3 ml mixture of 1.1 M sorbitol and YEPD (5:1), and grown for several hours to overnight in 28° C. shaker. The spores (1.5 ml) were added to 10 ml of Vogel's overlay agar containing 100 ppm of chlorimuron ethyl, and plated on Vogel's agar plates. The transformation plates were grown in a 28° C. incubator.

Screening of Transformants for Homologous Recombination at the cbh1 Locus—

Figure 6:
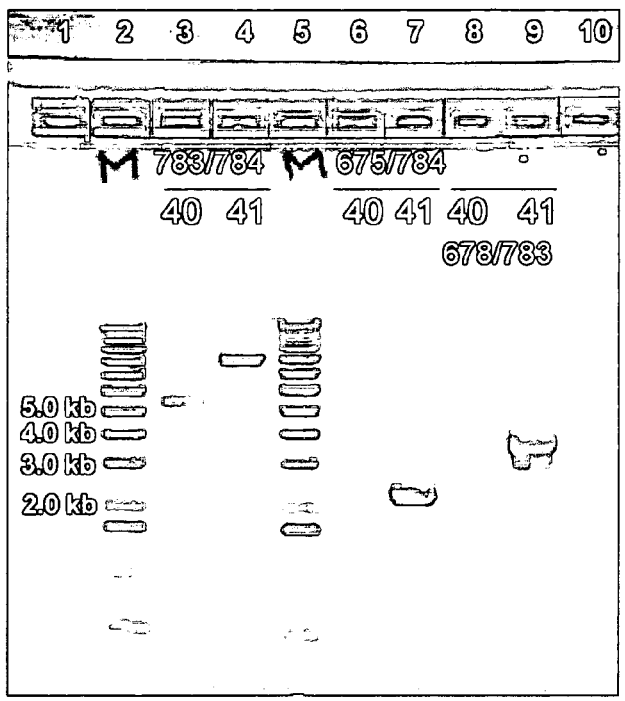
FIG. 6 depicts the homologous recombination of the deletion cassette at the cbh1 locus in transformant no 41.

Transformants showing stable morphology were grown in test tubes containing YEG (yeast extract with glucose) media to obtain mycelia samples for genomic DNA extraction. The genomic DNA extraction was performed following the protocol outlined by FastDNA Kit (Q-Biogene/MP Biosciences). PCR analysis was performed on the genomic DNA samples of the transformants to verify the occurrence of a homologous recombination event at the cbh1 locus resulting in the deletion of the cbh1 ORF. At least one transformant (#41) appeared to have a homologous deletion event at the cbh1 locus. A PCR product was absent for the reaction using primers SK853 (forward) 5'-GGATGGTGGCGTGAG-CAAG-3' (SEQ ID NO: 10) and SK854 (reverse) 5'-AGAGCTTCCAGTGGTAGTG-3' (SEQ ID NO:11), which amplifies a region in the cbh1 ORF (data not shown). Further analysis with primers pairs 1) SK783 (forward) 5'-CACGACCACTTTGATCTGC-3'SEQ ID NO:12) and SK784 (reverse) 5'-GTCAACACGTCTCCTATGTC-3' (SEQ ID NO:13), 2) 675R (forward) 5'-CGGCCCTGCAC-GAGTTCCT-3' (SEQ ID NO:14) and SK784 (reverse), and 3) pairs SK783 (forward) 5'-CACGACCACTTTGATCTGC-3'(SEQ ID NO:15) and 678R (reverse) 5'-CACGAGATGAT-GCTGCGACA-3' (SEQ ID NO:16) indicated that the deletion cassette had homologously recombined at the cbh1 locus (see FIG. 6). For these three PCR reactions transformant #40, which did not have a homologous recombination event at the cbh1 locus was used as a control. Primers SK783 and SK784 anneal outside of primers SK775 and SK778 in the genomic DNA sequence. Primers 675F and 678R anneal in the als marker. The PCR products were analyzed on 0.8% E-gels (Invitrogen).

Figure 7:
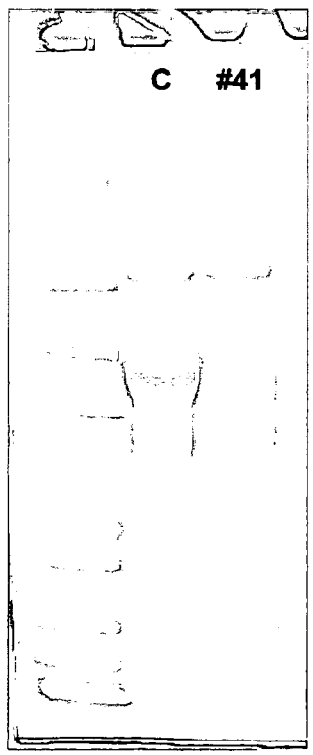
FIG. 7 illustrates an NuPAGE gel in which the cellulase protein (cbh1) is absent in transformant no. 41 as further described in example 4.

Additional data indicating the occurrence of the deletion of the cbh1 ORF in transformant #41 was the absence of the CBH1 protein when transformant #41 along with the parent strain were grown in shake flasks. Five-day cultures were taken and centrifuged. The supernatants were run on 4-12% NuPAGE gel (Invitrogen) with MOPS running buffer, and stained with SimplyBlue SafeStain (Invitrogen). The cbh1 protein, which runs approximately 60 kD on the NuPAGE gel with MOPS running buffer is absent in the sample of transformant #41 (FIG. 7).

Finally, it should be noted that there are alternative ways of implementing the present invention. Accordingly, the present embodiments are to be considered as illustrative and not restrictive, and the invention is not to be limited to the details given herein, but may be modified within the scope and equivalents of the appended claims. All publications and patents cited herein are incorporated by reference.

What is claimed is:

1. A method for introducing one or more nucleic acids into filamentous fungal spores to produce transformed fungal spores, comprising
mixing one or more filamentous fungal spores with one or more nucleic acids; and
applying an electric field under conditions that allow introduction of the one or more nucleic acids into one or more fungal spores, wherein the electric field is applied at a voltage of between about 15,500 V/cm and about 18,500 V/cm to produce filamentous fungal spores, wherein the electric field is applied with a device having a resistance of between 45Ω and 65Ω, wherein the electric field is applied at a capacitance of between 20 µF and 100 µF, wherein the number of transformants in a population is between about 400 transformants/µg DNA and about 5 transformants/µg DNA.

2. The method of claim 1, wherein the filamentous fungal spores are *Trichoderma* spores.

3. The method of claim 2, wherein the *Trichoderma* spores are *T. reesei* spores.

4. The method of claim 1, wherein the one or more nucleic acids in the mixture is at a concentration of between about 100 µg/ml and about 0.05 mg/ml.

5. The method of claim 1, wherein the one or more nucleic acids are mixed with the spores in a buffer and the ionic strength of the buffer is between about 0.0 mM and about 2.5 mM.

6. The method of claim 1, wherein when the electric field is applied with a device having a capacitance of 25 µF and the resistance of the device is about 50Ω.

7. The method of claim 1, further comprising culturing the fungal spores after introduction of the nucleic acids.

8. The method of claim 1, wherein the one or more nucleic acids comprise a gene of interest.

9. The method of claim 8, wherein the gene of interest encodes a protein of interest.

10. The method of claim 9, wherein the protein of interest is an endogenous or heterologous protein.

11. The method of claim 9, wherein the protein of interest is a secreted protein.

12. The method of claim 1, wherein the spores are collected by growing filamentous fungal cells in an appropriate medium for 5 to 15 days.

13. A method for introducing one or more nucleic acids into a population of filamentous fungal spores, comprising contacting a population of filamentous fungal spores with one or more nucleic acids to produce transformed fungal spores; and applying an electric field under conditions that allow introduction of the nucleic acids into the fungal spores, wherein the electric field is applied at a voltage of between about 15,000 V/cm and about 18,500 V/cm in the absence of lithium acetate, to produce transformed fungal spores, wherein the electric field is applied with a device having a resistance between 45Ω and 65Ω, wherein the electric field is applied at a capacitance of between 20 µF and about 100 µF, wherein the number of transformants in a population is between about 400 transformants/µg DNA and about 5 transformants/µg DNA, further comprising growing fungal cells for 5 to 15 days under conditions in which they sporulate before transformation.

14. The method of claim 13, wherein the fungal spores are *Trichoderma* spores.

15. The method of claim 13, wherein when the electric field is applied with a device having a capacitance of 25 µF and the resistance of the device is about 50Ω.

16. A method for introducing one or more nucleic acids into a population of *Trichoderma* spores to provide transformed *Trichoderma* spores,
comprising contacting a population of *Trichoderma* spores with one or more nucleic acids; and
applying an electric field of between 15,500 V/cm and about 18,500 V/cm under conditions that allow introduction of the one or more nucleic acids into the fungal spores to produce transformed *Trichoderma* fungal spores, wherein the electric field is applied with a device having a resistance of between 45Ω and 65Ω, wherein the electric field is applied at a capacitance of between 20 µF and about 100 µF, wherein the number of transformants in a population is between about 400 transformants/µg DNA and about 5 transformants/µg DNA.

17. The method of claim 16, wherein when the electric field is applied with a device having a capacitance of 25 µF and the resistance of the device is about 50Ω.

* * * * *